United States Patent
Samproni

(10) Patent No.: US 11,125,737 B2
(45) Date of Patent: Sep. 21, 2021

(54) MICROCAPILLARY SENSOR ARRAY

(71) Applicant: Siemens Healthcare Diagnostics Inc., Tarrytown, NY (US)

(72) Inventor: Jennifer Samproni, Braintree, MA (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 28 days.

(21) Appl. No.: 16/468,914

(22) PCT Filed: Dec. 13, 2017

(86) PCT No.: PCT/US2017/066035
§ 371 (c)(1),
(2) Date: Jun. 12, 2019

(87) PCT Pub. No.: WO2018/112008
PCT Pub. Date: Jun. 21, 2018

(65) Prior Publication Data
US 2019/0339252 A1    Nov. 7, 2019

Related U.S. Application Data

(60) Provisional application No. 62/435,329, filed on Dec. 16, 2016.

(51) Int. Cl.
*G01N 33/487* (2006.01)
*B01L 3/00* (2006.01)
(Continued)

(52) U.S. Cl.
CPC .... *G01N 33/48707* (2013.01); *B01L 3/50273* (2013.01); *B01L 3/502715* (2013.01); *G01N 27/3271* (2013.01); *G01N 27/333* (2013.01); *B01L 2300/024* (2013.01); *B01L 2300/0636* (2013.01); *B01L 2300/0663* (2013.01);
(Continued)

(58) Field of Classification Search
None
See application file for complete search history.

(56) References Cited

U.S. PATENT DOCUMENTS 8,287,807 B2    10/2012    Matsushita
8,911,367 B2    12/2014    Brister et al.
(Continued)

OTHER PUBLICATIONS

International Search Report and Written Opinion of International Application No. PCT/US2017/066035 dated Feb. 16, 2018.

*Primary Examiner* — J. Christopher Ball
(74) *Attorney, Agent, or Firm* — Dunlap Codding P.C.

(57) ABSTRACT

A microcapillary sensor array includes a sensor body that is elongated along a longitudinal axis. The sensor body has a first end, a second end spaced from the first end along the longitudinal axis, an outer surface, and an inner surface. The inner surface defines a hollow capillary that extends from the first end toward the second end along the longitudinal axis. The microcapillary sensor array includes a sensing element that extends through the sensor body from the outer surface to the hollow capillary and a conductive element in contact with the sensing element. The conductive element detects a response signal generated by a reaction between the sensing element and a fluid as the fluid flows through the hollow capillary contacting the sensing element.

19 Claims, 4 Drawing Sheets

(51) Int. Cl.
  *G01N 27/327*  (2006.01)
  *G01N 27/333*  (2006.01)
  *G01N 33/49*  (2006.01)

(52) U.S. Cl.
  CPC .................. *B01L 2300/0838* (2013.01); *B01L 2400/0406* (2013.01); *G01N 33/492* (2013.01); *G01N 33/4925* (2013.01)

(56) References Cited

U.S. PATENT DOCUMENTS

| | | | |
|---|---|---|---|
| 2002/0107227 A1* | 8/2002 | Cha ........................ | C12Q 1/002 514/100 |
| 2014/0218084 A1 | 7/2014 | Gumennik et al. | |
| 2015/0082874 A1* | 3/2015 | Samproni ............... | H05K 1/189 73/61.61 |
| 2016/0058341 A1 | 3/2016 | Heller et al. | |

* cited by examiner

MICROCAPILLARY SENSOR ARRAY

This application claims priority to U.S. Provisional Application No. 62/435,329, filed Dec. 16, 2016, the disclosure of which is hereby incorporated by reference in its entirety.

TECHNICAL FIELD

The present disclosure is directed to a microcapillary sensor array and a related system for analyzing a fluid.

BACKGROUND

Various types of tests related to patient diagnosis and therapy can be performed by analysis of a sample, such as a patient's bodily fluids, using automated sample analyzers. Such sample analyzers obtain measurements from the sample in order to determine the presence and/or amount of analyte of interest. In typical sample analyzers, as the number of analytes for detection increase the required sample volume increases. However, low sample volumes are desirable when the sample is limited, such as in the case of whole blood from neonatal patients, or when the sample itself is expensive. Although various known clinical analyzers for chemical, immunochemical and biological testing of samples are available, analytical clinical technology is challenged by increasing needs for improved levels of analysis while reducing sample volume requirements.

SUMMARY

An embodiment of the disclosure is a microcapillary sensor array. The microcapillary sensor array includes a sensor body that is elongated along a longitudinal axis. The sensor body has a first end, a second end spaced from the first end along the longitudinal axis, an outer surface, and an inner surface. The inner surface defines a hollow capillary that extends from the first end toward the second end along the longitudinal axis. The microcapillary sensor array includes a sensing element that extends through the sensor body from the outer surface to the hollow capillary and a conductive element in contact with the sensing element. The conductive element detects a response signal generated by a reaction between the sensing element and a fluid as the fluid flows through the hollow capillary contacting the sensing element.

Another embodiment of the present disclosure is a sample holding device. The sample holding device includes a microcapillary sensor array. The microcapillary sensor array includes a sensor body that is elongated along a longitudinal axis. The sensor body has a first end, a second end spaced from the first end along the longitudinal axis, an outer surface, and an inner surface. The inner surface defines a hollow capillary that extends from the first end toward the second end along the longitudinal axis. The microcapillary sensor array includes a sensing element that extends through the sensor body from the outer surface to the hollow capillary and a conductive element in contact with the sensing element. The conductive element detects response signals generated by the sensing element when a fluid flows through the hollow capillary and contacts the sensing element.

Another embodiment of the present disclosure is a system. The system includes a sample analyzer for analyzing a fluid, a microcapillary sensor array, and a computing device for analyzing electrical response signals generated by the microcapillary sensor array when the microcapillary sensor array is in contact with the fluid. The microcapillary sensor array includes a sensor body that is elongated along a longitudinal axis. The sensor body has a first end, a second end spaced from the first end along the longitudinal axis, an outer surface, and an inner surface. The inner surface defines a hollow capillary that extends from the first end toward the second end along the longitudinal axis. The microcapillary sensor array includes a sensing element that extends through the sensor body from the outer surface to the hollow capillary and a conductive element in contact with the sensing element. The conductive element detects response signals generated by the sensing element when a fluid flows through the hollow capillary and contacts the sensing element.

BRIEF DESCRIPTION OF THE DRAWINGS

The foregoing summary, as well as the following detailed description of illustrative embodiments of the present application, will be better understood when read in conjunction with the appended drawings. For the purposes of illustrating the present application, there is shown in the drawings illustrative embodiments of the disclosure. It should be understood, however, that the application is not limited to the precise arrangements and instrumentalities shown.

DETAILED DESCRIPTION OF ILLUSTRATIVE EMBODIMENTS

Figure 6:
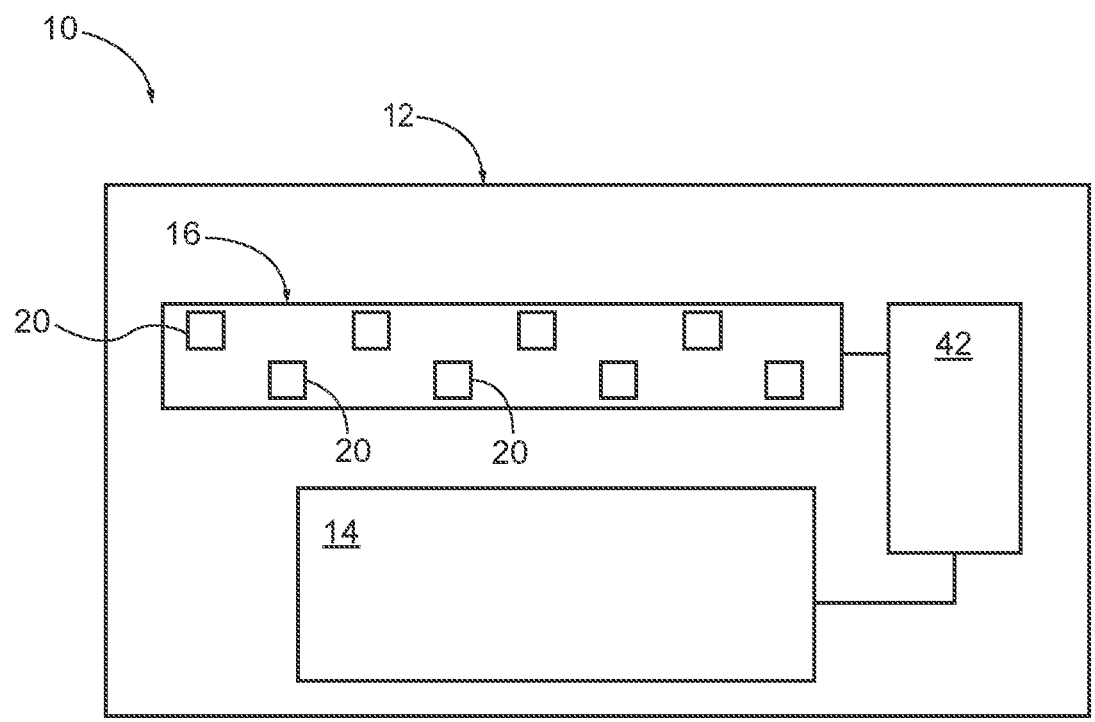
FIG. 6 is a schematic diagram of a system used to analyze a fluid including the microcapillary sensor shown in FIGS. 1A and 1B.

Embodiments of the present disclosure are directed to a microcapillary sensor array designed to detect various components and/or analytes in a fluid. The microcapillary sensor array 16 may form part of a sample test system 10. Turning initially to FIG. 6, the test system 10 includes a sample analyzer 12 configured to analyze signals generated by the microcapillary sensor array 16. The microcapillary sensor array 16 includes a plurality of sensing elements 20 that are configured to detect components and/or analytes of interest in a sample of the fluid. The sensing elements 20 are electrically responsive to a fluid and/or analytes produced by a fluid-reagent reaction. The microcapillary sensor array 16 may be used to test a sample of any particular fluid. For example, the fluid may a biological fluid, such as whole blood, plasma, pleural fluids, urine, and/or dialysate fluids or other fluids obtained from a patient. Furthermore, the fluid may also include non-biological sample liquids. The fluid is not limited strictly to liquids obtained from a patient.

Analytical tests conducted on the sample are implemented by the sample analyzer 12. The sample analyzer 12 has a computing device 14 and a plurality of transducers 42 electrically coupled to the sensing elements 20 and to the computing device 14. The transducers 42 forward electrical response signals generated by the microcapillary sensor array 16 to the computing device 14. The computing device 14 analyzes the electrical response signals generated by the microcapillary sensor array 16.

The computing device 14 includes electrical components that control operation of sample the analyzer 12 and implement analytical techniques for analyzing data generated by the microcapillary sensor array 16. The computing device 14 and its components provide an interface for the user to control operation of the sample analyzer 12. In one example, the computing device 14 has a processing portion (e.g. a computer processor and/or a controller), a memory portion, an input-output portion, a user interface, and one or more software applications. The software application executes instructions for controlling operation of the sample analyzer 12 and its components. The software applications also analyze signals generated by the microcapillary sensor array 16. The computing device 14 may also be configured as a controller. In such an embodiment, the controller may include one or more processors, memory, and input/output links.

The sample analyzer 12 may include dispensing equipment (not shown) used to deliver a sample of fluid to the microcapillary sensor array 16. The dispensing equipment may include a motor that powers and an arm controlled by the motor. The arm is adapted to deliver the sample of fluid to the microcapillary sensor array 16 via a pipe, tube, cartridge, insert, or other device for holding a sample. In another embodiment, the dispensing equipment can deliver sample of fluid directly to the microcapillary sensor array 16. In one example, the arm is moveable to deliver the sample of fluid to the microcapillary sensor array 16. Alternatively, the microcapillary sensor array 16 is moveable relative to a fixed arm to receive the sample of fluid. The computing device 14 may include a software application that when executed by the computer processor controls operation of the dispensing equipment.

Figure 1A:
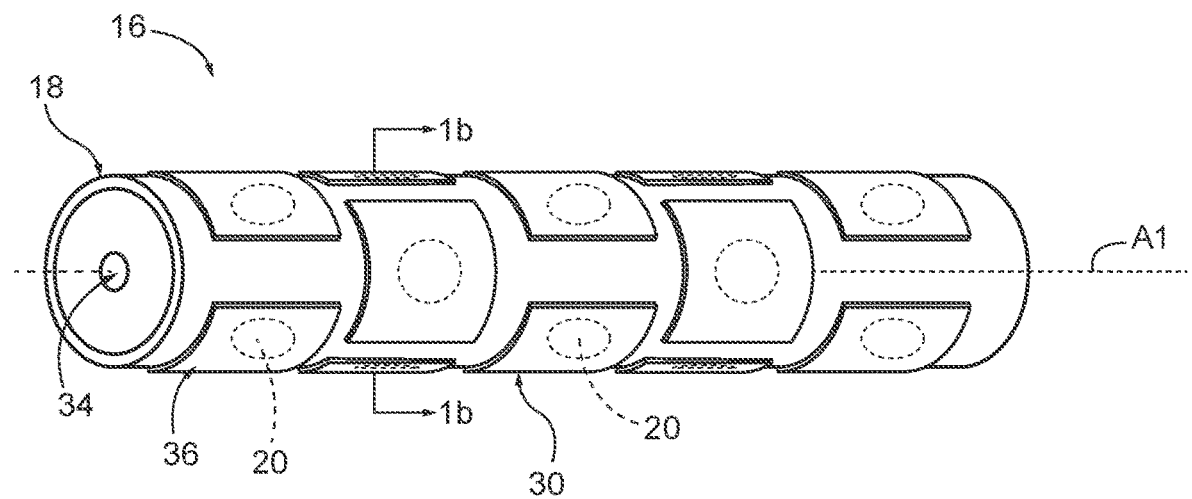
FIG. 1A is a perspective view of a microcapillary sensor used in a sample analysis system according to an embodiment of the present disclosure.
Figure 1B:
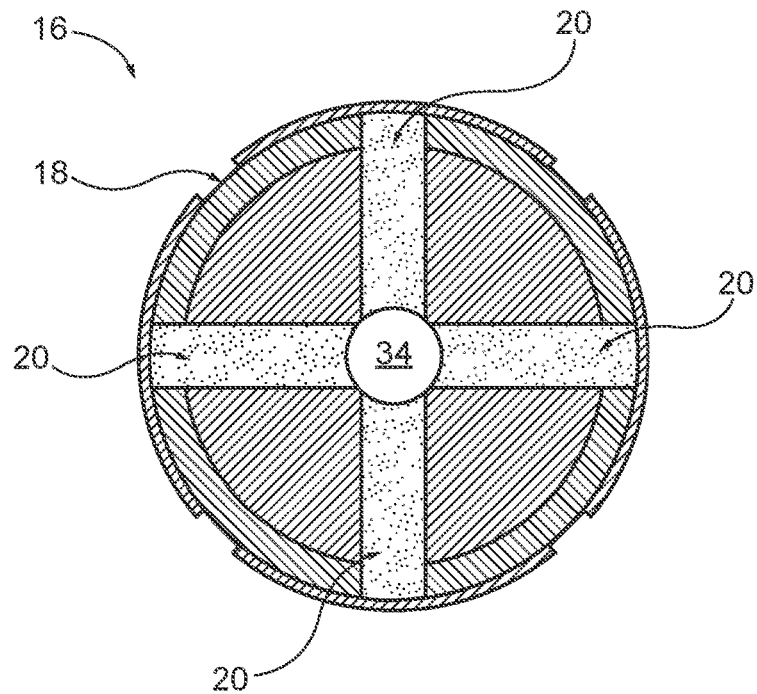
FIG. 1B is a cross-sectional view of the microcapillary taken in along line 1*b*-1*b* in FIG. 1B.

Referring to FIGS. 1A and 1B, the microcapillary sensor array 16 includes a sensor body 18, a hollow capillary 34 extending through the sensor body 18, a plurality of sensing elements 20 open to the hollow capillary 34, and a plurality of conductive elements 36. The conductive elements 36 can detect and forward the response signal generated by the sensing elements to the transducers 42 (transducers 42 shown in FIG. 6) and/or the computing device 14.

Figure 2:
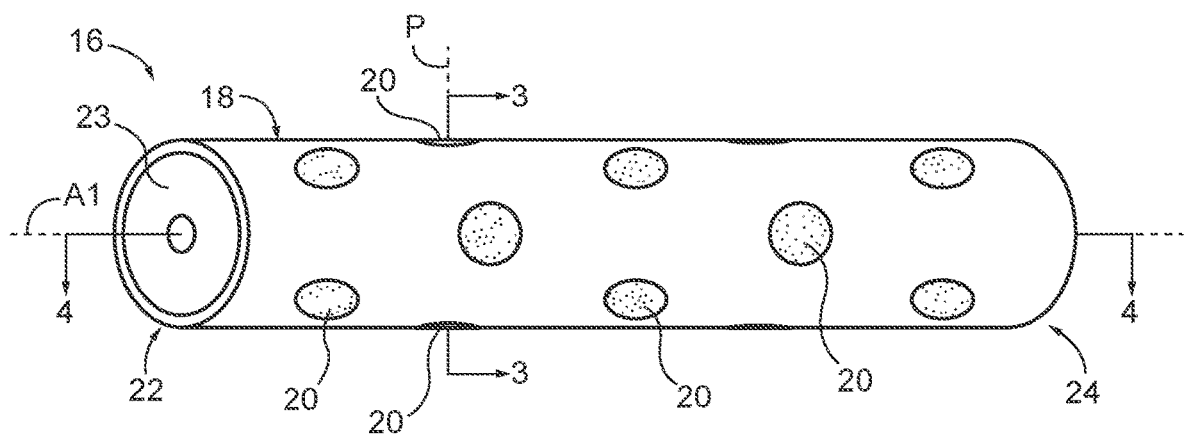
FIG. 2 is a perspective view of a microcapillary shown in FIGS. 1A and 1B with the outer conductive elements removed.
Figure 3:
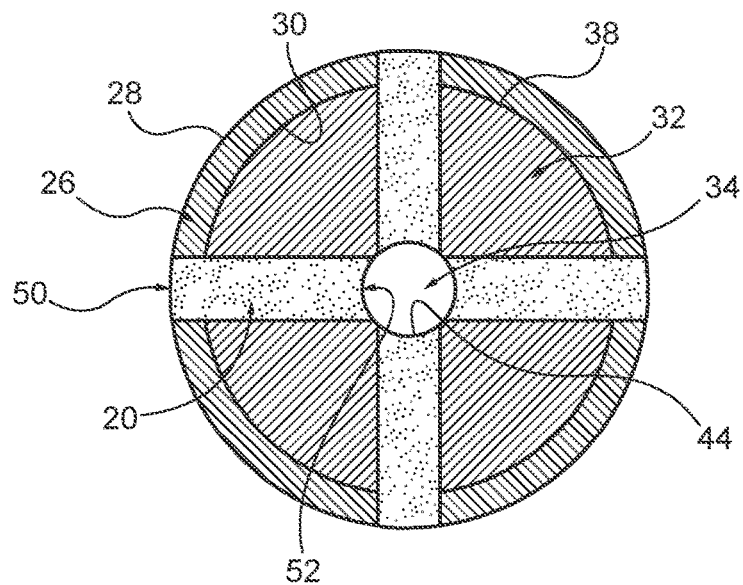
FIG. 3 is a cross-sectional view of the microcapillary taken in along line 3-3 in FIG. 2.
Figure 4:
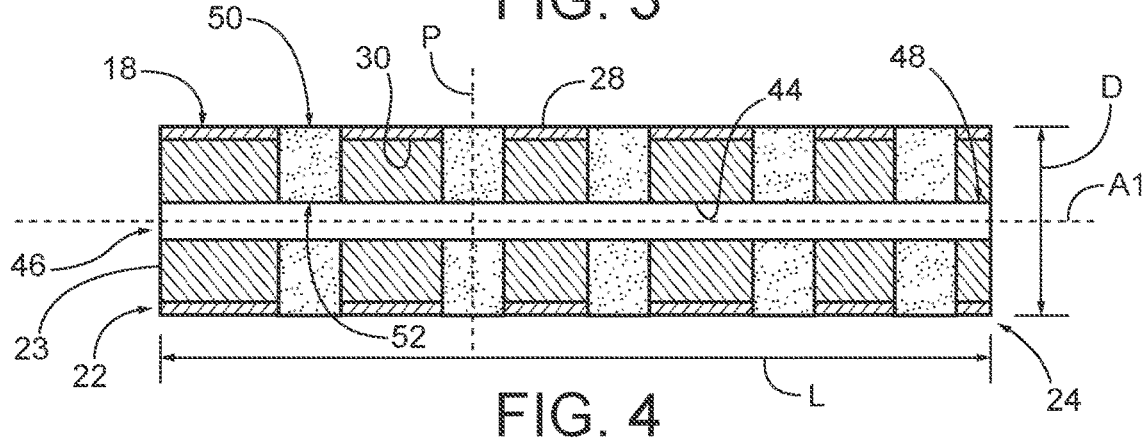
FIG. 4 is a cross-sectional view of the microcapillary taken along line 4-4 in FIG. 2.

FIGS. 2-4 illustrate a sensor body 18 constructed in accordance with the inventive concepts disclosed herein. The sensor body 18 comprises an outer surface 28 and an inner surface 44. The hollow capillary 34 extends along and is defined by the inner surface 44. In the embodiment shown, the sensor body 18 includes an outer sheath 26, a substrate core 32 within the outer sheath 26, and the hollow capillary 34 encased by the substrate core 32. The sensor body 18 is shown with the outer sheath and substrate core as separate components. In alternative embodiment, the outer sheath 26 and substrate core 32 can be a monolithic component of the sensor body 18.

Continuing with FIGS. 2-4, the sensor body 18 is elongate along a longitudinal axis A1. As shown, the sensor body 18 has a first end 22 and a second end 24 spaced from the first end along the longitudinal axis A1. The hollow capillary 34 extends from the first end 22 toward the second end 24 along the longitudinal axis A1. The first end 22 of the sensor body 18 defines a sensor face 23 that may be positioned to contact the fluid during the test. The second end 24 of the sensor body 18 is where the fluid could possible exit the sensor body 18. When the sensor face 23 contacts the fluid, the fluid may flow into the hollow capillary 34 via capillary action. For instance, the fluid enters the hollow tube 34 without assistance of an external force or draw. Alternatively, the hollow capillary 34 can be configured to draw fluid with the assistance of an external force from a syringe or other similar device. In some examples, fluid can enter through sensor face 23 and exit the second end 24. The sensor body 18 further defines a length L that extends from the first end 22 to the second end 24 along the longitudinal axis A1. As shown, the sensor body 18 has a cross-sectional dimension D that is perpendicular to the length L (and longitudinal axis A1). In one example, the cross-sectional dimension D may be between 0.10 mm to about 2.0 mm. The cross-sectional dimension D may, however, fall outside the state ranges. The sensor body 18 may be in the form of a cylindrical tube. However, the sensor body 18 may have any particular cross-sectional shape and the present disclosure is not limited to cylindrical sensor body 18.

Referring to FIGS. 2-4, the outer sheath 26 defines an outer surface 28 and a inner surface 30 that is opposite to the outer surface 28. The outer sheath 26 surrounds the substrate core 32. The outer sheath 26 may be any material sufficient to contain the substrate core 32. The outer sheath 26 may be formed from glass, a polymer, or a ceramic material such as an oxide of aluminum, silicon or boron. Suitable materials are well known to those skilled in the art. In one embodiment, the outer sheath 26 is a flexible material. Nonlimiting examples of suitable flexible materials include paper, polyethylene terephthalate (PET), polyethylene (PE), polyimide (PI), polyether ether ketone (PEEK), and the like.

The substrate core 32 has an outer surface 38 and an inner surface 44 that is opposite to the outer surface 38. The inner surface 44 of the substrate core 32 defines the hollow capillary 34. The outer surface 38 of the substrate core 32 is adjacent to the inner surface 30 of the outer sheath 26. The substrate core 32 may be formed from glass, a polymer, or a ceramic material such as an oxide of aluminum, silicon or boron. Suitable materials are well known to those skilled in the art. In one embodiment, the outer sheath 26 is a flexible material. Nonlimiting examples of suitable flexible materials include paper, polyethylene terephthalate (PET), polyethylene (PE), polyimide (PI), polyether ether ketone (PEEK), and the like.

In some embodiments, the sensor body 18 may include either the outer sheath 26 or the substrate core 32, but not both. In an example without a substrate core 32, the outer sheath 26 can be thick enough to define a suitable hollow capillary 34 and contain the sensing elements 20 as described below. In an alternative example, without the outer sheath 28, the substrate core 32 contains the sensing elements 20 as further described below.

The hollow capillary 34 extends throughout the length L of the sensor body 18 and is in contact with the substrate core 32. In the embodiment shown, the hollow capillary 34 has a first end 46 and a second end 48. The first end 46 is proximate and/or partially defines the sensor face 23. Furthermore, the hollow capillary 34 may be centrally disposed within the sensor body 18. In such an example, the hollow capillary 34 is coaxial with the longitudinal axis A1. In alternative embodiments, the hollow capillary 34 may be laterally offset with respect to the longitudinal axis A1.

Continuing with FIGS. 2-4, the microcapillary sensor array 16 includes a plurality of sensing elements 20. The sensing elements 20 react with analytes in the fluid and generate a response signal. The response signal is usually a type of electro-magnetic signal. To achieve this function, the sensing element 20 may be any membrane material that is responsive to a fluid or analyte generated by a fluid-reagent reaction. The sensing element material may be an ion selective membrane. Suitable ion selective membranes may include an ionophore and a polymer, such as polyvinyl alcohol, polyvinyl chloride, polyvinyl acetate, and/or polyacrylamide, or any other suitable polymer. In some instances, the membrane may include suitable enzymes and/or other components responsive to a particular analyte and/or fluid. When fluid contacts the sensing elements 20, the sensing elements 20 can generate a response signal that is sent to the computing device 14 for analysis.

As shown, the sensing elements 20 extend through sensor body 18 to the hollow capillary 34. Each sensing element includes an outer end 50 aligned with the outer surface 28 and an inner end 52 that is aligned with inner surface 44. The inner end 52 is open to the hollow capillary 34. As shown, the sensing elements are substantially linear and extend along a radial direction that is perpendicular to the axis A1. However, the sensing elements 20 can be curvilinear and/or non-orthogonal with respect to the axis A1. The sensing elements 20 may be disposed around the hollow capillary 34 in a number of different configurations. In one example, one set of sensing elements 20 are disposed circumferentially around the axis A1. Furthermore, one or more sensing elements 20 are aligned along a plane P that is perpendicular to the axis A1. In another example, the sensing element 20 may be aligned on different planes P such that each sensing element 20 is spaced apart with respect to each other in a direction that is parallel to the axis A1. Thus, the sensing elements 20 can be stacked along the longitudinal axis A1.

The microcapillary sensor array 16 may be modified to include as many sensing elements 20 as needed. For example, the microcapillary sensor array 16 may have 1 sensing element 2 sensors up to 12 sensing element. However, the microcapillary sensor array 16 is not limited to 12 sensors. The microcapillary sensor array 16 may have more than 12 sensors to detect any number of different analytes as needed. Furthermore, the microcapillary sensor array 16 may have duplicate sensors.

Referring back to FIGS. 1A and 1B, the conductive elements 36 transmits electric response signals to the transducers 42 and/or the computing device 14. The conductive elements 36 may be any conductive material, such as a wire, rod, cable, pin, pad, patch, or the like. The conductive elements 36 can be formed from gold, silver, copper and aluminum metals and alloys thereof, carbon nanotube bundles, and/or another other type of conductive material. The conductive elements 36 may be contacts points which can be coupled to the computing device 14 by placing them in contact with wires, paths, etc., which are coupled to the computing device 14. In other words, conductive elements 36 transmit the response signals from the respective sensors 20, via electrical connection, to the computing device 14.

The microcapillary sensor array 16 may can detect a range of analytes. The electrically responsive components of the sensor(s)—the substrate cores—are responsive to fluid upon contact with the fluid. Such fluid responsive sensors may be used to detect a variety of analytes of interest, such as blood gas analytes (e.g. pH, $pCO_2$, $pO_2$), electrolytes (Na+, K+, Ca++, Cl−), metabolites (Glucose, Lactate), CO-oximetry (tHb, HHb, $O_2Hb$, $sO_2$, COHb, MetHb), and/or neonatal total bilirubin.

The microcapillary sensor array 16 is adapted to detect various combinations of analyte types. For instance, the sensor array may be adapted to detect a different analyte of interest. In still another variation, the sensor array 16 may be adapted to detect the same analytes. In accordance with the illustrated embodiment, a first set of sensing elements 20 may be electrically responsive to a first analyte, and a second set of sensing elements 20 may be electrically responsive to a second analyte. In one example, each sensing element 20 is responsive to similar analytes (i.e. the first and second analytes are the same analytes). Constructing the sensor array 16 to include sensing elements 20 that detect similar analytes provides detection redundancy, thereby improving the reliability of the sensor array 16 for that particular analyte. In another example, each sensing element is responsive to different analytes (i.e. the first, second and third analytes are different analytes). Utilizing sensing elements designed for different analytes increases the breadth of tests available to perform on the sample of fluid.

Referring back to FIGS. 1A and 1B, microcapillary sensor array 16 is configured to utilize relatively low sample volumes. The size of the hollow capillary 34 can be selected for the required sample volume while the plurality of sensing elements 20 make it is possible to test for a wide range analytes. Furthermore, using the hollow capillary 34 with circumferential and/or stacked sensing elements 20 can also reduce the sample volume required to complete the desired analysis. Because of the relatively small sizes of the microcapillary sensor array 16 described herein and the potentially large number of sensing elements 20 that can be used, large analyte panels can be obtained with relatively low sample volume, such as 100 μl or less. A low sample volume can be less than 100 μl, 80 μl, 80 μl, 40 μl, or 20 μl.

Figure 5:
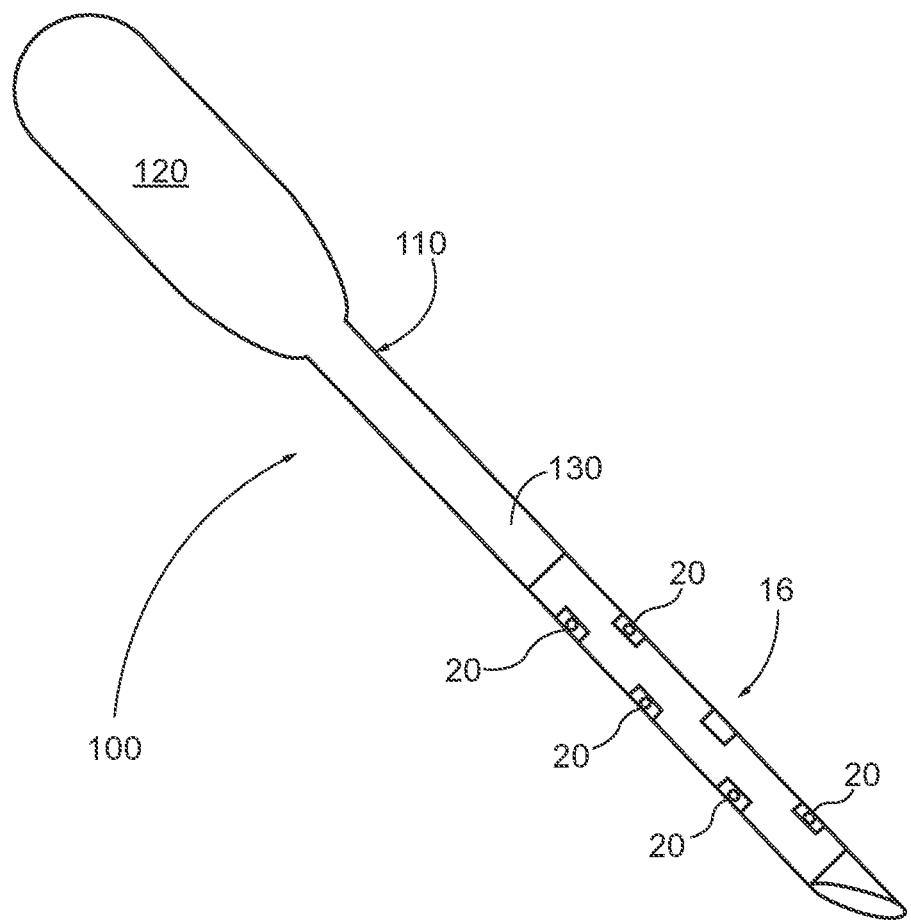
FIG. 5 is a perspective view of a pipette including a microcapillary sensor shown in FIGS. 1A-4.

Another embodiment of the present disclosure includes a sample holding device 100 that includes a microcapillary sensor array 16 as described herein. A sample holding device can include a device body adapted to hold and/or transport a fluid. The device body can be a test tube, vial, syringe, pipette, cartridge, needle, or any other similar device that can extract and/or hold a fluid. In one exemplary embodiment shown in FIG. 5, a pipette 110 may include a handle or vessel portion 120 and elongate capillary 130 that draws sample fluid into the vessel portion 120. The elongate capillary 130 may include a microcapillary sensor array 16 as described herein. As fluid is drawn into the pipette 110 through the elongate capillary 130, the fluid contacts the sensing elements 20, which detect analytes in the fluid. In another embodiment, the sensor 16 may be integrated into a needle (such as a micro needle sensors array), which can be used to obtain blood directly from the patient. As such, illustrative micro needle arrays may be suitable for at-home use. Accordingly, the microcapillary sensor array 16 may form part of any device that includes a lumen or tube for the transport or holding of fluid. The sample holding devices may include electrical circuitry, such as transducers 42, conductive elements 36, and/or electrical interfaces for engaging a port in a device and/or sample analyzer. In such an example, the sample holding device may be able draw and or hold the sample while also provide a sensing functionality that allow direct interface with sample analyzer. This, in turn, may reduce complexity and operation of sample analyzers while also simplifying user controlled test procedures.

Manufacture of the microcapillary sensor array 16 involves first forming the sensor body 18. The sensor body 18 may be extruded, injection molded, or manufactured using additive manufacturing process. Either during or after formation of the sensor body, a plurality of channels may be formed into the sensor body 18. The channels may be formed via laser etching or other techniques. The sensing elements 20 can be filled into the respective channels. For example, a membrane solution is inserted into channels. The membrane solution may cure or solidify into the sensing elements 20. The hollow capillary 34 can be formed into the sensor body 18. Conductive elements 36 are then formed or applied directly to the sensor body 18 so that the conductive elements 36 are in contact with the sensing elements 20. In an alternative embodiment, after the sensor body 18 is formed with a hollow capillary 34 and the plurality of channels. Next, a flexible substrate having a plurality of sensing elements 20 on one side and conductive elements 36 on the other side is wrapped around the sensor body 18 so that the sensing elements 20 register into the plurality of channels. The microcapillary sensor array 16 may be assembled into a sample holding device and/or positioned in the test area of the sample analyzer 12

In use, a sample of fluid is obtained and is inserted into the sample analyzer 12. The fluid contacts the sensor face 23 of the microcapillary sensor array 16. Capillary action draws the fluid into the hollow capillary 34 and into contact with sensing elements 20. Each sensing element 20, in turn, generates a response signal that is transmitted to the transducers 42. The transducers 42, in turn, forward signals to the computing device 14. The computing device 14 determines the analyte(s) present in the fluid based on the characteristics of the received signal.

The inventive concepts are not limited in their application to the details of construction and the arrangement of the components set forth in the description or illustrated in the drawings. The inventive concepts disclosed herein are capable of other embodiments or of being practiced or carried out in various ways. Also, it is to be understood that the phraseology and terminology employed herein is for the purpose of description and should not be regarded as limiting the inventive concepts disclosed and claimed herein in any way.

Numerous specific details are set forth in order to provide a more thorough understanding of the inventive concepts. However, it will be apparent to one of ordinary skill in the art that the inventive concepts within the instant disclosure may be practiced without these specific details. In other instances, well-known features have not been described in detail to avoid unnecessarily complicating the instant disclosure.

As used herein, the terms "comprises," "comprising," "includes," "including," "has," "having" or any other variation thereof, are intended to cover a nonexclusive inclusion. For example, a composition, a process, method, article, or apparatus that comprises a list of elements is not necessarily limited to only those elements but may include other elements not expressly listed or inherently present therein.

As used herein the terms "approximately," "about," "substantially" and variations thereof are intended to include not only the exact value qualified by the term, but to also include some slight deviations therefrom, such as deviations caused by measuring error, manufacturing tolerances, wear and tear on components or structures, stress exerted on structures, and combinations thereof, for example.

Unless expressly stated to the contrary, "or" refers to an inclusive or and not to an exclusive or. For example, a condition A or B is satisfied by anyone of the following: A is true (or present) and B is false (or not present), A is false (or not present) and B is true (or present), and both A and B are true (or present). An inclusive or may be understood as being the equivalent to: at least one of condition A or B.

In addition, use of the "a" or "an" are employed to describe elements and components of the embodiments herein. This is done merely for convenience and to give a general sense of the inventive concepts. This description should be read to include one or at least one and the singular also includes the plural unless it is obvious that it is meant otherwise.

Any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

The invention claimed is:

1. A microcapillary sensor array, comprising:
   a sensor body elongated along a longitudinal axis, the sensor body having a first end, a second end spaced from the first end along the longitudinal axis, an outer surface, an inner surface, and a channel extending between the outer surface, and the inner surface, wherein the inner surface defines a hollow capillary that extends from the first end toward the second end along the longitudinal axis;
   a sensing element having an outer end and an inner end, the sensing element extends through the channel in the sensor body from the outer surface of the sensor body to the inner surface of the sensor body such that the outer end of the sensing element is at the outer surface of the sensor body and the inner end of the sensing element is at the inner surface of the sensor body; the sensing element being a membrane material that is responsive to a fluid or analyte generated by a fluid-reagent reaction; and
   a conductive element in contact with the sensing element;
   wherein the conductive element detects a response signal generated by a reaction between the sensing element and a fluid as the fluid flows through the hollow capillary contacting the sensing element.

2. The microcapillary sensor array of claim 1, wherein the sensing element is comprised of an electrically responsive material.

3. The microcapillary sensor array of claim 1, wherein the sensing element is a plurality of sensing elements that are responsive to different analytes.

4. The microcapillary sensor array of claim 1, wherein the sensing element is a plurality of sensing elements that are responsive to similar analytes.

5. The microcapillary sensor array of claim 1, wherein the sensing element has at least one enzyme configured to be responsive to a pre-determined analyte to generate a response signal.

6. The microcapillary sensor array of claim 5, wherein the sensor body comprises:
   an outer sheath that defines the outer surface; and
   a substrate core within the outer sheath, wherein the substrate core defines the inner surface such that the hollow capillary extends through the substrate core.

7. The microcapillary sensor array of claim 1, wherein a first sensing element is aligned on a first plant that is perpendicular to the longitudinal axis and a second sensing element is aligned on a second place that is perpendicular to the longitudinal axis.

8. The microcapillary sensor array of claim 1, wherein multiple sensing elements are disposed around the hollow capillary.

9. The microcapillary sensor array of claim 1, wherein the hollow capillary extends entirely through the sensor body.

10. The microcapillary sensor array of claim 1, further comprising a transducer associated the sensing element, wherein the transducer is electrically coupled to the conductive element.

11. The microcapillary sensor array of claim 1, wherein the sensing element is a plurality of sensing elements.

12. The microcapillary sensor array of claim 11, wherein the conductive element is a plurality of conductive elements.

13. The microcapillary sensor array of claim 12, further comprising a plurality of transducers associated with the plurality of sensing elements, wherein the plurality of transducers are electrically coupled to the plurality of conductive elements.

14. A sample vessel comprising the microcapillary sensor array according to claim 1.

15. A sample holding device, comprising:
a microcapillary sensor array comprising: a sensor body elongated along a longitudinal axis, the sensor body having a first end, a second end spaced from the first end along the longitudinal axis, an outer surface, an inner surface, and a plurality of channels extending between the outer surface and the inner surface, wherein the inner surface defines a hollow capillary that extends from the first end toward the second end along the longitudinal axis;
a plurality of sensing elements with each sensing element having an outer end and an inner end, each sensing element extending through one of the respective channels in the sensor body from the outer surface of the sensor body to the inner surface of the sensor body such that the outer end of each sensing element is at the outer surface of the sensor body and the inner end of the sensing element is at the inner surface of the sensor body, each of the sensing elements being, independently, a membrane material that is responsive to a fluid or analyte generated by a fluid-reagent reaction; and
a plurality of conductive elements with a conductive element in contact with each sensing element;
wherein the conductive element detects a response signal generated by a reaction between the sensing element and a fluid as the fluid flows through the hollow capillary contacting the sensing element; and
a plurality of transducers coupled to the sensing elements.

16. The sample holding device of claim 15, further comprising an interface that is electrically coupled to the plurality of transducers, wherein the interface is adapted to engage a computing device or a sample analyzer.

17. The sample holding device of claim 15, further comprising:
a body, including a vessel portion and an elongate capillary portion configured to draw fluid into the vessel portion, the elongate capillary portion housing the microcapillary sensor array such that fluid being drawn into the vessel portion is configured to contact at least one sensing element.

18. A system, comprising:
a) a sample analyzer for analyzing a fluid;
b) a microcapillary sensor array:
a sensor body elongated along a longitudinal axis, the sensor body having a first end, a second end spaced from the first end along the longitudinal axis, an outer surface, an inner surface, and a plurality of channels extending between the outer surface and the inner surface, wherein the inner surface defines a hollow capillary the extends from the first end toward the second end along the longitudinal axis;
a sensing element having an outer end and an inner end, the sensing element extending through at least one channel in the sensor body from the outer surface of the sensor body to the inner surface of the sensor body, the sensing element being a membrane material that is responsive to a fluid or analyte generated by a fluid-reagent reaction; and
c) a computing device for analyzing electrical response signals generated by the microcapillary sensor array when the microcapillary sensor array is in contact with the fluid.

19. A method for analyzing a fluid, comprising the steps of:
receiving, by a computing device, a plurality of electrical response signals generated by a microcapillary sensor array when the microcapillary sensor array is in contact with the fluid, the microcapillary sensor array comprising:
a sensor body elongated along a longitudinal axis, the sensor body having a first end, a second end spaced from the first end along the longitudinal axis, and outer surface, an inner surface, and a plurality of channels extending between the outer surface and the inner surface, wherein the inner surface defines a hollow capillary that extends from the first end toward the second end along the longitudinal axis;
a sensing element having an outer end and an inner end, the sensing element extending through at least one channel in the sensor body from the outer surface of the sensor body to the inner surface of the sensor body, the sensing element being a membrane material that is responsive to a fluid or analyte generated by a fluid-reagent reaction; and,
analyzing, by the computing device, the plurality of electrical response signals generated by the microcapillary sensor array to determine at least one analyte in the fluid.

* * * * *